United States Patent
Cheng

(10) Patent No.: US 9,293,024 B2
(45) Date of Patent: Mar. 22, 2016

(54) SITTING POSTURE DETECTION AND REMINDER MECHANISM FOR A TOILET

(71) Applicant: Kohler (China) Investment Co. Ltd., Shanghai (CN)

(72) Inventor: Ho-Tzu Cheng, Shanghai (CN)

(73) Assignee: KOHLER (CHINA) INVESTMENT CO. LTD., Shanghai (CN)

( * ) Notice: Subject to any disclaimer, the term of this patent is extended or adjusted under 35 U.S.C. 154(b) by 0 days.

(21) Appl. No.: 14/560,256

(22) Filed: Dec. 4, 2014

(65) Prior Publication Data
US 2015/0379852 A1 Dec. 31, 2015

(30) Foreign Application Priority Data
Jun. 30, 2014 (CN) .......................... 2014 1 0305282

(51) Int. Cl.
G08B 23/00 (2006.01)
G08B 21/04 (2006.01)

(52) U.S. Cl.
CPC .................................. *G08B 21/0446* (2013.01)

(58) Field of Classification Search
CPC ............................ G08B 21/0446; G08B 21/04
USPC ............ 340/573.7, 573.1; 600/473, 594, 587, 600/595; 4/234, 254, 300
See application file for complete search history.

(56) References Cited

U.S. PATENT DOCUMENTS

| | | | | |
|---|---|---|---|---|
| 6,673,027 B2 * | 1/2004 | Fischer | .................. | A61B 5/103 600/595 |
| 8,978,171 B1 * | 3/2015 | Wise | ...................... | A47K 13/24 4/254 |
| 2009/0324024 A1 * | 12/2009 | Worthington | .......... | A61B 5/103 382/118 |
| 2010/0257663 A1 * | 10/2010 | Willner | .................. | A47K 17/02 4/254 |
| 2015/0113719 A1 * | 4/2015 | Good | .................... | A47K 17/028 4/254 |
| 2015/0142381 A1 * | 5/2015 | Fitzsimmons | ......... | A47C 7/006 702/166 |

* cited by examiner

*Primary Examiner* — Toan N Pham
(74) *Attorney, Agent, or Firm* — Foley & Lardner LLP

(57) ABSTRACT

Systems and methods are provided for detecting a sitting posture of a user on toilet and generating notifications for the user based on the detected sitting posture. A sitting posture detection and reminder mechanism measures a distance X between a distance sensor and a body of the user sitting on the toilet. The mechanism calculates an angle α between the user's spine and the user's thighs based on the measured distance X and generates a sitting posture notification for the user based on the calculated angle α. The mechanism may operate a motor coupled to the toilet cover to automatically adjust an angle of the cover and guide the user into a healthy sitting posture.

20 Claims, 3 Drawing Sheets

SITTING POSTURE DETECTION AND REMINDER MECHANISM FOR A TOILET

CROSS-REFERENCE TO RELATED PATENT APPLICATIONS

This application claims the benefit of and priority to Chinese Invention Application No. 201410305282.6, filed Jun. 30, 2014, the entirety of which is incorporated by reference herein.

FIELD OF INVENTION

The present invention relates generally to the field of toilet accessories. More particularly, the present invention relates to a sitting posture detection and reminder mechanism for a toilet.

BACKGROUND

A squatting posture may be healthier for a user than a sitting posture at the time of defecation. In a squatting posture, the muscles of the colon may be completely relaxed to promote defecation and avoid a complication of colorectal cancer. Conventional squatting pans achieve the effect of a squatting posture by elevating the height of the user's thighs. However, such squatting pans can have the side effect of inhibiting blood circulation, thereby causing a feeling of numbness in the user's legs.

SUMMARY

The present invention provides systems and methods for detecting a sitting posture of a toilet user and generating notifications for the user based on the detected sitting posture. Advantageously, the systems and methods of the present disclosure may be used to determine whether the sitting posture of the user is healthy at the time of defecation and may provide feedback and alerting information to the user to remind the user of the healthy posture.

One implementation of the present disclosure is a sitting posture detection and reminder mechanism for a toilet. The mechanism includes a distance sensor configured to measure a distance X between the distance sensor and a body of a user sitting on the toilet, a control module configured to calculate an angle α between the user's spine and the user's thighs based on the measured distance X and to generate a control signal based on the calculated angle α, and a reminder module configured to receive the control signal from the control module and to generate a sitting posture notification for the user upon receiving the control signal.

In some embodiments, the distance sensor is installed at a distance H above the toilet and the control module calculates the angle α according to the formula $$\tan(\alpha) = \frac{H}{X}.$$

In some embodiments, the distance sensor is installed on a body of the toilet and configured to measure the distance X at an angle γ above horizontal and the control module calculates the angle α according to the formula $$\tan(\alpha) = \frac{X\sin(\gamma)}{X\cos(\gamma) - d},$$

where d is a stored horizontal distance between the distance sensor and a center of a seat of the toilet.

In some embodiments, the control module is configured to send a first control signal to the reminder module when the calculated angle α is within a predetermined range, and send a second control signal to the reminder module when the calculated angle α is not within the predetermined range. The second control signal may be different from the first control signal. In some embodiments, the predetermined range is between 35° and 65°.

In some embodiments, the reminder module is configured to generate a first sitting posture notification for the user in response to receiving the first control signal. The first sitting posture notification may indicate that the user currently has a healthy defecation posture.

In some embodiments, the reminder module is configured to generate a second sitting posture notification for the user in response to receiving the second control signal. The second sitting posture notification may indicate that the user currently does not have a healthy defecation posture.

In some embodiments, the control module is configured to send a third control signal to the reminder module when the calculated angle α exceeds a threshold value. In some embodiments, the threshold value is approximately 65°.

The reminder module may be a forced reminder module configured to operate a motor coupled to a cover of the toilet in response to receiving the third control signal. Operating the motor may include causing rotation of a shaft coupling the cover to the toilet and adjusting an angle β of the cover relative to vertical such that the angle β is within a predetermined range. In some embodiments, the angle β is complementary to the angle α and the predetermined range for the angle β is between 25° and 55°.

Another implementation of the present disclosure is method for detecting and using a sitting posture of a user on a toilet. The method includes measuring a distance X between a distance sensor and a body of the user sitting on the toilet, calculating an angle α between the user's spine and the user's thighs based on the measured distance X, and generating a sitting posture notification for the user based on the calculated angle α.

In some embodiments, the distance sensor is installed at a distance H above the toilet and the angle α is calculated according to the formula $$\tan(\alpha) = \frac{H}{X}.$$

In some embodiments, the distance sensor is installed on a body of the toilet and configured to measure the distance X at an angle γ above horizontal and the angle α is calculated according to the formula $$\tan(\alpha) = \frac{X\sin(\gamma)}{X\cos(\gamma) - d},$$

where d is a stored horizontal distance between the distance sensor and a center of a seat of the toilet.

In some embodiments, the method includes determining whether the calculated angle α is within a predetermined range and generating a first sitting posture notification for the user when the calculated angle α is within the predetermined range. The first sitting posture notification may indicate that the user currently has a healthy defecation posture. In some embodiments, the predetermined range is between 35° and 65°.

In some embodiments, the method includes determining whether the calculated angle α is within the predetermined range and generating a second sitting posture notification for the user when the calculated angle α is not within the predetermined range. The second sitting posture notification may indicate that the user currently does not have a healthy defecation posture.

In some embodiments, the method includes determining whether the calculated angle α exceeds a threshold value and operating a motor coupled to a cover of the toilet when the calculated angle α exceeds the threshold value. The threshold value may be approximately 65°.

In some embodiments, operating the motor includes causing rotation of a shaft coupling the cover to the toilet and adjusting an angle β of the cover relative to vertical such that the angle β is within a predetermined range. In some embodiments, the angle β is complementary to the angle α and the predetermined range for the angle β is between 25° and 55°.

DESCRIPTION OF REFERENCE NUMBERS IN THE DRAWINGS

Figure 1:
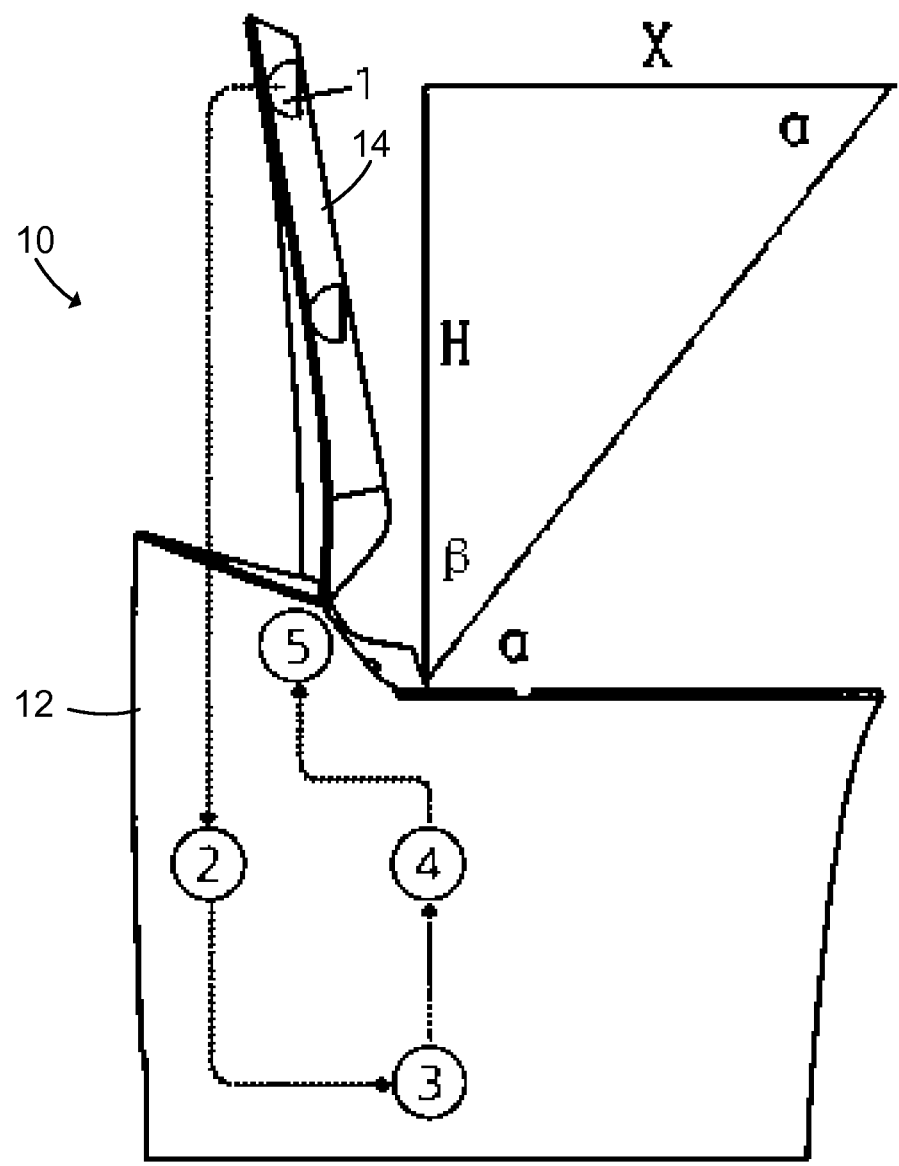
FIG. 1 is a schematic diagram of a sitting posture detection and reminder mechanism for a toilet, according to an exemplary embodiment.

| | |
|---|---|
| 1: Distance sensor | 2: Control module |
| 3: Reminder module | 4: Forced reminder module |
| 5: Motor | 10: Sitting posture detection and reminder mechanism |
| 12: Toilet base | 14: Toilet cover |

DETAILED DESCRIPTION

Referring generally to the FIGURES, a sitting posture detection and reminder mechanism 10 for a toilet 12 and components thereof are shown, according to various exemplary embodiments. Mechanism 10 may be configured to detect a sitting posture of a toilet user, determine whether the detected sitting posture is healthy (e.g., by comparing the detected posture to one or more stored sitting postures), and provide feedback and/or alerting information to the user based on a result of the determination.

Sitting posture detection and reminder mechanism 10 is shown to include a distance sensor 1 and a control module 2. In various embodiments, mechanism 10 may include a reminder module 3 and/or a forced reminder module 4. Distance sensor 1 may be configured to measure a distance between a human body (e.g., a user of toilet 12) and distance sensor 1. Distance sensor 1 may send a distance signal representing the distance measurement to control module 2. Control module 2 may send a control signal to reminder module 3 and/or forced reminder module 4. Forced reminder module 4 may control the rotational position of toilet cover 14 by operating a motor 5 coupled to a rotation shaft attached to cover 14.

As shown in FIG. 1, distance sensor 1 may be installed above toilet 12 (e.g., attached to cover 14 or a tank for toilet 12) in some embodiments. Distance sensor 1 may be positioned at a height H above toilet 12 when cover 14 is lifted. Distance sensor 1 may be any type of distance or proximity sensor (e.g., capacitive, displacement, Doppler effect, Eddy-current, inductive, magnetic, optical, photocell, ultrasonic, etc.) and may use any type of distance sensing technology to measure a distance X between sensor 1 and a human body. Distance sensor 1 may send the measured distance value X to control module 2.

Control module 2 may include a processing circuit having a processor and memory. The processor may be a general purpose or specific purpose processor, an application specific integrated circuit (ASIC), one or more field programmable gate arrays (FPGAs), a group of processing components, or other suitable processing components. The processor may be configured to execute computer code or instructions stored in the memory or received from other computer readable media. The memory may include one or more devices (e.g., memory units, memory devices, storage devices, etc.) for storing data and/or computer code for completing and/or facilitating the various processes described in the present disclosure. The memory may include random access memory (RAM), read-only memory (ROM), hard drive storage, temporary storage, non-volatile memory, flash memory, optical memory, or any other suitable memory for storing software objects and/or computer instructions. The memory may include database components, object code components, script components, or any other type of information structure for supporting the various activities and information structures described in the present disclosure. The memory may be communicably connected to the processor via the processing circuit and may include computer code for executing (e.g., by the processor) one or more processes described herein.

Still referring to FIG. 1, control module 2 may be configured to calculate an angle α between the spine and thighs of a user sitting on toilet 12 according to the following formula:

$$\tan(\alpha) = \frac{H}{X}$$

where H is the height of distance sensor 1 relative to the body of toilet 12 when cover 14 is lifted and X is the measured horizontal distance between distance sensor 1 and the human body. For embodiments in which distance sensor 1 is located on cover 14, distance X may represent the horizontal distance between toilet cover 14 (e.g., the top of cover 14 when lifted) and the human body.

In some embodiments, mechanism 10 may include a plurality of distance sensors installed proximate to toilet 12 (e.g., on toilet cover 14, on a tank for toilet 12, etc.). The plurality of distance sensors may be distributed along the height H between the base of toilet 12 and the top of cover 14 when lifted. Each distance sensor may be configured to measure a horizontal distance (e.g., $X_1, X_2, \ldots, X_n$) to the human body at a different height above toilet 12 (e.g., $H_1, H_2, \ldots, H_n$).

Control module 2 may calculate a plurality of angles (e.g., $\alpha_1$, $\alpha_2, \ldots, \alpha_n$) using a stored height for each distance sensor and the distance measured by each distance sensor. Control module 2 may average two or more of the calculated angles $\alpha_1$, $\alpha_2, \ldots, \alpha_n$ to more precisely determine the angle $\alpha$ between the spine and thighs of a toilet user.

Control module 2 may compare the calculated angle $\alpha$ with a threshold value or threshold range to determine whether the user of toilet 12 has a healthy posture. In some embodiments, the threshold range is approximately 35°-65°. In other embodiments, the threshold range may have greater or lesser bounds. If the calculated angle $\alpha$ is within the threshold range (e.g., $35° \le \alpha \le 65°$), control module 2 may send a first control signal to reminder module 3. In response to receiving the first control signal, reminder module 3 may generate a first alert or notification (e.g., a first alerting sound, vibration, display, etc.) indicating that the user currently has a healthy defecation posture. However, if the calculated angle $\alpha$ is not within the threshold range (e.g., $\alpha < 35°$ or $\alpha > 65°$), control module 2 may send a second control signal to reminder module 3. In response to receiving the second control signal, reminder module 3 may generate a second alert or notification (e.g., a second alerting sound, vibration, display, etc.) indicating that the user currently does not have a healthy defecation posture.

Figure 2:
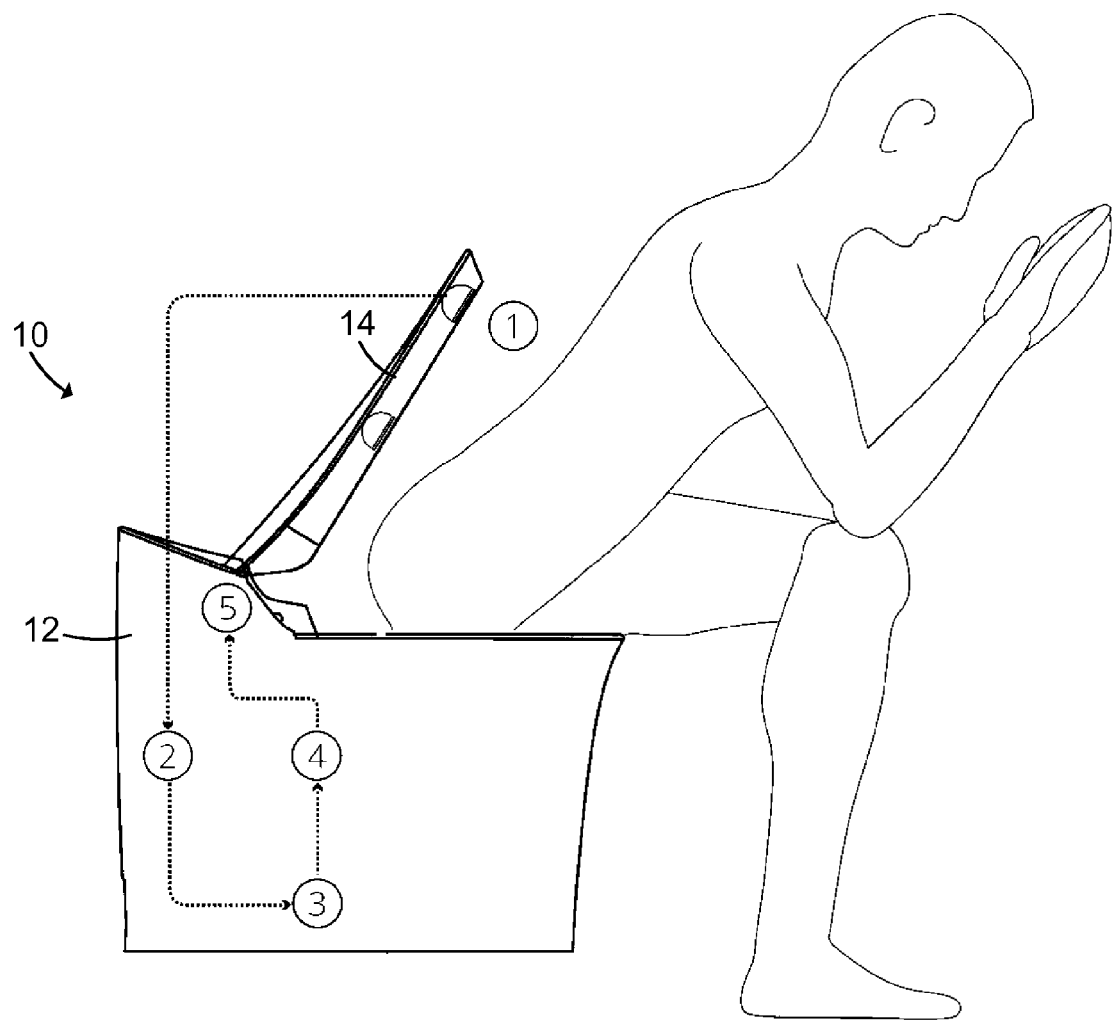
FIG. 2 is a schematic diagram of a working state for a forced reminder module of the mechanism of FIG. 1, according to an exemplary embodiment.

Still referring to FIG. 1, in some embodiments, mechanism 10 includes a forced reminder module 4. Forced reminder module 4 may be configured to adjust the rotational position of cover 14 (e.g., by operating motor 5 coupled to a rotation shaft of cover 14) to guide the user into a healthy defecation posture. For example, if the calculated angle $\alpha$ is greater than an upper bound of the threshold range (e.g., $\alpha > 65°$), control module 2 may send a control signal to forced reminder module 4. Forced reminder module 4 may control the angle $\beta$ of cover 14 relative to vertical. In some embodiments, angles $\alpha$ and $\beta$ are complementary (e.g., $\alpha + \beta = 90°$). Forced reminder module 4 may adjust angle $\beta$ such that $\alpha$ is within the threshold range or less than an upper bound of the threshold range. For example, forced reminder module 4 may adjust the position of cover 14 until angle $\beta$ is between 35° and 65° (e.g., $35° \le \beta \le 65°$), thereby guiding the human body into the optimal defecation angle, as shown in FIG. 2.

Figure 3:
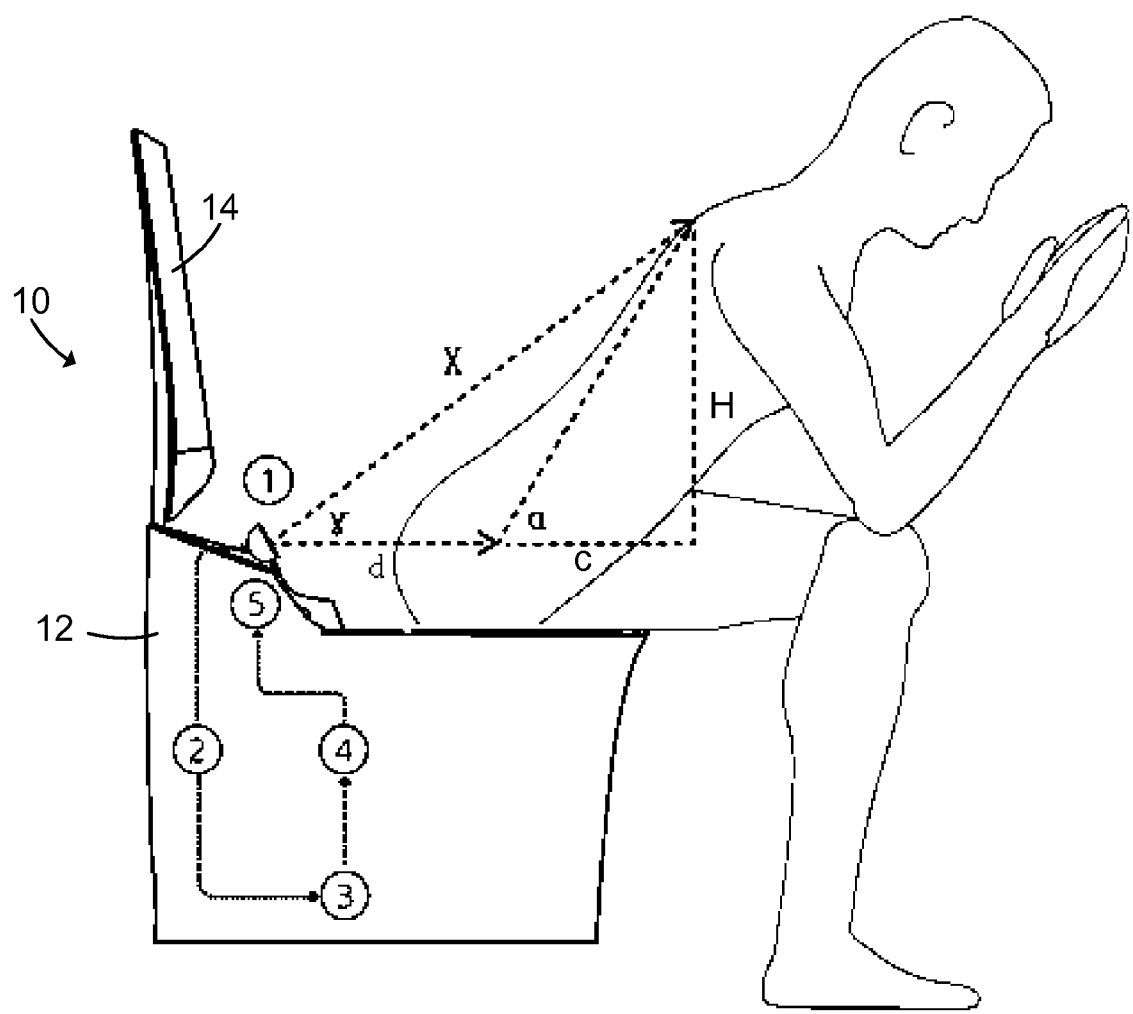
FIG. 3 is a schematic diagram of another sitting posture detection and reminder mechanism for a toilet, according to an exemplary embodiment.

As shown in FIG. 3, distance sensor 1 may be installed on the body or base of toilet 12 in some embodiments. Distance sensor 1 may be oriented at a predetermined angle $\gamma$ above horizontal and configured to measure a distance X between the human body and distance sensor 1 at the angle $\gamma$. Distance sensor 1 may send the measured distance X to control module 2.

Control module 2 may calculate the angle $\alpha$ between the spine and the thighs of the user according to the following formula:

$$\tan(\alpha) = \frac{X\sin(\gamma)}{X\cos(\gamma) - d}$$

where X is the linear distance between distance sensor 1 and the human body at the angle $\gamma$, angle $\gamma$ is the angle that distance sensor 1 is oriented above horizontal, and d is the horizontal distance between distance sensor 1 and the pivot point of the user's hips. In some embodiments, distance d is the known distance between distance sensor 1 and the center of the toilet seat. The quantity $X \sin(\gamma)$ represents the vertical distance H along the right side of the right triangle shown in FIG. 3 and the quantity $X \cos(\gamma) - d$ represents the horizontal distance c along the bottom of the right triangle. Once the angle $\alpha$ is calculated, control module 2, reminder module 3, and forced reminder module 4 may perform the functions described with reference to FIG. 1.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A sitting posture detection and reminder mechanism for a toilet, the mechanism comprising:
    a distance sensor configured to measure a distance X between the distance sensor and a body of a user sitting on the toilet;
    a control module configured to calculate an angle $\alpha$ between a user's spine and a user's thighs based on the measured distance X and to generate a control signal based on the calculated angle $\alpha$; and
    a reminder module configured to receive the control signal from the control module and to generate a sitting posture notification for the user upon receiving the control signal.

2. The mechanism of claim 1, wherein:
    the distance sensor is installed at a distance H above the toilet; and
    the control module calculates the angle $\alpha$ according to $$\tan(\alpha) = \frac{H}{X}.$$

3. The mechanism of claim 1, wherein:
    the distance sensor is installed on a body of the toilet and configured to measure the distance X at an angle $\gamma$ above horizontal; and
    the control module calculates the angle $\alpha$ according to $$\tan(\alpha) = \frac{X\sin(\gamma)}{X\cos(\gamma) - d},$$

where d is a stored horizontal distance between the distance sensor and a center of a seat of the toilet.

4. The mechanism of claim 1, wherein the control module is configured to:
    send a first control signal to the reminder module when the calculated angle $\alpha$ is within a predetermined range; and
    send a second control signal, different from the first control signal, to the reminder module when the calculated angle $\alpha$ is not within the predetermined range.

5. The mechanism of claim 4, wherein the predetermined range is between 35° and 65°.

6. The mechanism of claim 4, wherein the reminder module is configured to generate a first sitting posture notification for the user in response to receiving the first control signal, the first sitting posture notification indicating that the user currently has a healthy defecation posture.

7. The mechanism of claim 4, wherein the reminder module is configured to generate a second sitting posture notification for the user in response to receiving the second control signal, the second sitting posture notification indicating that the user currently does not have a healthy defecation posture.

8. The mechanism of claim 1, wherein the control module is configured to send a third control signal to the reminder module when the calculated angle α exceeds a threshold value.

9. The mechanism of claim 8, wherein the reminder module is a forced reminder module configured to operate a motor coupled to a cover of the toilet in response to receiving the third control signal.

10. The mechanism of claim 9, wherein operating the motor comprises:
causing rotation of a shaft coupling the cover to the toilet; and
adjusting an angle β of the cover relative to vertical such that the angle β is within a predetermined range.

11. The mechanism of claim 10, wherein:
the angle β is complementary to the angle α; and
the predetermined range for the angle β is between 25° and 55°.

12. A method for detecting and using a sitting posture of a user on a toilet, the method comprising:
measuring a distance X between a distance sensor and a body of the user sitting on the toilet;
calculating an angle α between a user's spine and a user's thighs based on the measured distance X; and
generating a sitting posture notification for the user based on the calculated angle α.

13. The method of claim 12, wherein:
the distance sensor is installed at a distance H above the toilet; and
wherein calculating the angle α comprises calculating α according to $$\tan(\alpha) = \frac{H}{X}.$$

14. The method of claim 12, wherein:
the distance sensor is installed on a body of the toilet and configured to measure the distance X at an angle γ above horizontal; and
wherein calculating the angle α comprises calculating α according to $$\tan(\alpha) = \frac{X\sin(\gamma)}{X\cos(\gamma) - d},$$

where d is a stored horizontal distance between the distance sensor and a center of a seat of the toilet.

15. The method of claim 14, further comprising:
determining whether the calculated angle α is within a predetermined range; and
generating a first sitting posture notification for the user when the calculated angle α is within the predetermined range, the first sitting posture notification indicating that the user currently has a healthy defecation posture.

16. The method of claim 14, further comprising:
determining whether the calculated angle α is within a predetermined range; and
generating a second sitting posture notification for the user when the calculated angle α is not within the predetermined range, the second sitting posture notification indicating that the user currently does not have a healthy defecation posture.

17. The method of claim 15 or 16, wherein the predetermined range is between 35° and 65°.

18. The method of claim 12, further comprising:
determining whether the calculated angle α exceeds a threshold value; and
operating a motor coupled to a cover of the toilet when the calculated angle α exceeds the threshold value.

19. The mechanism of claim 18, wherein operating the motor comprises:
causing rotation of a shaft coupling the cover to the toilet; and
adjusting an angle β of the cover relative to vertical such that the angle β is within a predetermined range.

20. The mechanism of claim 19, wherein:
the angle β is complementary to the angle α; and
the predetermined range for the angle β is between 25° and 55°.

* * * * *